(12) United States Patent
Ribault et al.

(10) Patent No.: US 9,410,181 B2
(45) Date of Patent: Aug. 9, 2016

(54) METHOD AND UNIT FOR PREPARING A SAMPLE FOR THE MICROBIOLOGICAL ANALYSIS OF A LIQUID

(75) Inventors: Sebastien Ribault, Romanswiller (FR); Gael Waiche, Molsheim (FR)

(73) Assignee: EMD Millipore Corporation, Billerica, MA (US)

( * ) Notice: Subject to any disclaimer, the term of this patent is extended or adjusted under 35 U.S.C. 154(b) by 1284 days.

(21) Appl. No.: 11/805,539

(22) Filed: May 23, 2007

(65) Prior Publication Data

US 2007/0298451 A1   Dec. 27, 2007

(30) Foreign Application Priority Data

Jun. 27, 2006   (FR) ...................... 06 05796

(51) Int. Cl.
  *C12Q 1/24*   (2006.01)
  *C12M 1/34*   (2006.01)
  *G01N 1/40*   (2006.01)

(52) U.S. Cl.
  CPC .......... *C12Q 1/24* (2013.01); *G01N 2001/4088* (2013.01)

(58) Field of Classification Search
  USPC ........................................... 435/4, 30, 288.1
  IPC .................... C12Q 1/24; C12M 1/34
  See application file for complete search history.

(56) References Cited

U.S. PATENT DOCUMENTS

| | | |
|---|---|---|
| 2,923,669 A | 2/1960 | Poitras ....................... 195/103.5 |
| 3,211,645 A | 10/1965 | Ferrari |
| 3,556,302 A | 1/1971 | Agranat |
| 3,565,973 A | 2/1971 | Michaels |
| 3,632,507 A | 1/1972 | Witt |
| 3,702,806 A | 11/1972 | Oliva |
| 3,737,377 A | 6/1973 | Sternberg |
| 3,859,212 A | 1/1975 | Smalley et al. |
| 3,968,037 A | 7/1976 | Morgan et al. |
| 4,045,377 A | 8/1977 | Pearson |
| 4,055,469 A | 10/1977 | Snoke et al. |
| 4,200,695 A | 4/1980 | Chong et al. |
| 4,215,198 A | 7/1980 | Gordon ........................... 435/31 |
| 4,305,829 A | 12/1981 | Kelsey et al. |
| 4,317,726 A * | 3/1982 | Shepel ........................... 210/236 |
| 4,359,537 A | 11/1982 | Chong |
| 4,371,674 A | 2/1983 | Hertel et al. |
| 4,380,590 A | 4/1983 | Chong |
| 4,382,028 A | 5/1983 | Paget |
| 4,450,078 A | 5/1984 | Walker et al. |
| 4,515,893 A | 5/1985 | Kung et al. |
| 4,528,933 A | 7/1985 | Allen |
| 4,536,294 A | 8/1985 | Guillet et al. |
| 4,676,980 A | 6/1987 | Segal et al. |
| 4,780,409 A | 10/1988 | Monji et al. |
| 4,816,567 A | 3/1989 | Cabilly et al. |
| 4,828,701 A | 5/1989 | Cussler |
| 4,839,046 A | 6/1989 | Chandler |
| 4,863,613 A | 9/1989 | Johnson et al. |
| 4,904,385 A | 2/1990 | Wessling et al. |
| 4,912,032 A | 3/1990 | Hoffman et al. |
| 4,925,785 A | 5/1990 | Wang et al. |
| 4,968,435 A | 11/1990 | Neff et al. |
| 5,003,047 A | 3/1991 | Yarmush et al. |
| 5,047,511 A | 9/1991 | Mehrotra |
| 5,091,178 A | 2/1992 | Hellstrom et al. |
| 5,091,313 A | 2/1992 | Chang |
| 5,116,754 A | 5/1992 | Fraser et al. ................ 435/252.1 |
| 5,139,031 A * | 8/1992 | Guirguis ........................ 600/584 |
| 5,152,903 A | 10/1992 | Neff et al. |
| 5,164,057 A | 11/1992 | Mori et al. |
| 5,171,450 A | 12/1992 | Hoots |
| 5,208,161 A | 5/1993 | Saunders et al. |
| 5,238,545 A | 8/1993 | Yoshioka et al. |
| 5,258,122 A | 11/1993 | Ha et al. |
| 5,324,787 A | 6/1994 | Pinschmidt et al. |
| 5,340,865 A | 8/1994 | Neff et al. |
| 5,342,581 A | 8/1994 | Sanadi |

(Continued)

FOREIGN PATENT DOCUMENTS

| | | |
|---|---|---|
| EP | 0162034 B1 | 11/1990 |
| EP | 0534016 A1 | 3/1993 |
| EP | 0420937 B1 | 11/1994 |
| EP | 0720937 B1 | 11/1994 |
| EP | 0922715 A2 | 6/1999 |
| EP | 0851768 B1 | 4/2002 |
| EP | 1923461 A1 | 5/2008 |
| GB | 2 297 926 | 8/1996 |
| GB | 2305936 A | 4/1997 |
| JP | 5-95778 A | 4/1993 |

(Continued)

OTHER PUBLICATIONS

French Search Report dated Jun. 2, 2009 in co-pending U.S. Appl. No. 12/459,879.

(Continued)

*Primary Examiner* — Kagnew H Gebreyesus
*Assistant Examiner* — Paul Martin
(74) *Attorney, Agent, or Firm* — Nields, Lemack & Frame, LLC

(57) ABSTRACT

The preparation unit comprises a body (2) within which are fixed a first (3) and a second (4) membrane, said first membrane (3) having a first predetermined pore diameter and said second membrane (4) a second predetermined pore diameter smaller than said first predetermined pore diameter of said first membrane (3), said body also comprising means (16, 20) for retrieving said sample collected on said second membrane (4).

The method of preparing such a sample comprises the step of procuring such a preparation unit (1), the step of passing a predetermined volume of said liquid through said first membrane and through said second membrane (4) in order to collect a sample on said second membrane (4); and the step of retrieving said sample so collected on said second membrane (4).

8 Claims, 4 Drawing Sheets

(56) References Cited

U.S. PATENT DOCUMENTS

| | | |
|---|---|---|
| 5,354,481 A | 10/1994 | Neff et al. |
| 5,354,801 A | 10/1994 | O'Toole et al. |
| 5,374,971 A | 12/1994 | Clapp et al. |
| 5,430,110 A | 7/1995 | Ahlers et al. |
| 5,512,480 A | 4/1996 | Sandstrom et al. |
| 5,525,519 A | 6/1996 | Woiszwillo |
| 5,573,675 A | 11/1996 | Sommese et al. |
| 5,599,719 A | 2/1997 | Woiszwillo |
| 5,622,700 A | 4/1997 | Jardieu et al. |
| 5,622,857 A | 4/1997 | Goffe |
| 5,672,347 A | 9/1997 | Aggarwal et al. |
| 5,684,107 A | 11/1997 | Schneider et al. |
| 5,693,762 A | 12/1997 | Queen et al. |
| 5,714,338 A | 2/1998 | Waifei et al. |
| 5,721,108 A | 2/1998 | Robinson et al. |
| 5,725,856 A | 3/1998 | Hudziak et al. |
| 5,728,559 A | 3/1998 | Nilsson et al. |
| 5,733,507 A | 3/1998 | Zakim |
| 5,736,137 A | 4/1998 | Anderson et al. |
| 5,739,383 A | 4/1998 | Yoon et al. |
| 5,770,358 A | 6/1998 | Dower et al. |
| 5,807,489 A | 9/1998 | Farinato et al. |
| 5,840,804 A | 11/1998 | Carl et al. |
| 5,840,851 A | 11/1998 | Plomer et al. |
| 5,846,816 A | 12/1998 | Forth |
| 5,879,564 A | 3/1999 | Farinato |
| 5,929,214 A | 7/1999 | Peters et al. |
| 5,994,560 A | 11/1999 | Yoon et al. |
| 5,998,588 A | 12/1999 | Hoffman et al. |
| 6,024,955 A | 2/2000 | Asano et al. |
| 6,127,526 A | 10/2000 | Blank |
| 6,133,047 A | 10/2000 | Elaissari et al. |
| 6,139,746 A | 10/2000 | Kopf |
| 6,147,176 A | 11/2000 | Neff et al. |
| 6,153,104 A | 11/2000 | Robertson et al. |
| 6,191,242 B1 | 2/2001 | Ryles et al. |
| 6,197,522 B1 | 3/2001 | Keller et al. |
| 6,221,655 B1 | 4/2001 | Fung et al. |
| 6,245,555 B1 | 6/2001 | Curtis |
| 6,258,275 B1 | 7/2001 | Freitag et al. |
| 6,294,622 B1 | 9/2001 | Barajas et al. |
| 6,300,142 B1 | 10/2001 | Andrewes et al. |
| 6,307,013 B1 | 10/2001 | Chivers et al. |
| 6,358,730 B1 | 3/2002 | Kane |
| 6,367,749 B2 | 4/2002 | Valiulis |
| 6,372,141 B1 | 4/2002 | Okano et al. |
| 6,374,684 B1 | 4/2002 | Dority |
| 6,420,487 B1 | 7/2002 | Vaidya et al. |
| 6,454,950 B1 | 9/2002 | Tjerneld et al. |
| 6,521,341 B1 | 2/2003 | Elaissari et al. |
| 6,534,633 B1 | 3/2003 | Weidanz et al. |
| 6,538,089 B1 | 3/2003 | Samra et al. |
| 6,544,424 B1 | 4/2003 | Shevitz |
| 6,565,872 B2 | 5/2003 | Wu et al. |
| 6,582,926 B1 | 6/2003 | Chilkoti |
| 6,638,918 B2 | 10/2003 | Davison et al. |
| 6,641,735 B1 | 11/2003 | Yoshizako et al. |
| 6,673,598 B1 | 1/2004 | Akers et al. |
| 6,689,836 B2 | 2/2004 | Vaidya et al. |
| 6,706,187 B1 | 3/2004 | Okano et al. |
| 6,709,862 B2 | 3/2004 | Curtis |
| 6,716,593 B1 | 4/2004 | Robins et al. |
| 6,737,235 B1 | 5/2004 | Cros et al. |
| 6,765,081 B2 | 7/2004 | Lin et al. |
| 6,770,758 B2 | 8/2004 | Pan et al. |
| 6,805,793 B2 | 10/2004 | Yoshizako et al. |
| 6,821,515 B1 | 11/2004 | Cleland et al. |
| 6,830,670 B1 | 12/2004 | Viovy et al. |
| 6,852,819 B2 | 2/2005 | Ohnishi et al. |
| 6,858,694 B2 | 2/2005 | Ohnishi et al. |
| 6,863,437 B2 | 3/2005 | Ohnishi et al. |
| 6,867,268 B2 | 3/2005 | Vaidya et al. |
| 6,926,832 B2 | 8/2005 | Collins et al. |
| 6,956,077 B1 | 10/2005 | Akiyama et al. |
| 6,967,085 B1 | 11/2005 | Hughes et al. |
| 6,974,660 B2 | 12/2005 | Manias et al. |
| 7,001,953 B2 | 2/2006 | Chen et al. |
| 7,011,930 B2 | 3/2006 | Manias et al. |
| 7,012,136 B2 | 3/2006 | Yamanaka et al. |
| 7,052,917 B1 | 5/2006 | Ohnishi et al. |
| 7,070,696 B2 | 7/2006 | Weir et al. |
| 7,083,948 B1 | 8/2006 | Sassenfeld et al. |
| 7,157,603 B2 | 1/2007 | Hilbrig |
| 7,160,971 B2 | 1/2007 | Mallapragada et al. |
| 7,169,908 B2 | 1/2007 | Lester et al. |
| 7,195,925 B2 | 3/2007 | Ohnishi et al. |
| 7,300,545 B2 | 11/2007 | Ohara et al. |
| 7,355,020 B2 | 4/2008 | Yamanaka et al. |
| 7,377,686 B2 | 5/2008 | Hubbard |
| 7,393,698 B2 | 7/2008 | Furukawa et al. |
| 7,422,724 B1 | 9/2008 | Manginell et al. |
| 7,429,458 B2 | 9/2008 | Chilkoti |
| 7,442,515 B2 | 10/2008 | Ratner et al. |
| 7,514,007 B2 | 4/2009 | Chen et al. |
| 7,541,167 B2 | 6/2009 | Dave et al. |
| 7,547,747 B2 | 6/2009 | Hashimoto et al. |
| 7,553,658 B2 | 6/2009 | Kepka et al. |
| 7,625,764 B2 | 12/2009 | Stayton et al. |
| 7,632,656 B2 | 12/2009 | Kanazawa et al. |
| 7,695,905 B2 | 4/2010 | Furukawa et al. |
| 7,767,399 B2 | 8/2010 | Murphy et al. |
| 8,133,457 B2 | 3/2012 | Ribault et al. |
| 8,163,886 B2 | 4/2012 | Moya |
| 8,241,591 B2 | 8/2012 | Ribault et al. |
| 8,263,343 B2 | 9/2012 | Hallgren et al. |
| 8,362,217 B2 | 1/2013 | Moya et al. |
| 8,569,464 B2 | 10/2013 | Moya et al. |
| 8,691,918 B2 | 4/2014 | Jaber et al. |
| 8,915,374 B2 | 12/2014 | Franks et al. |
| 8,999,702 B2 | 4/2015 | Kelly et al. |
| 9,090,930 B2 | 7/2015 | Ribault et al. |
| 9,174,860 B2 | 11/2015 | Franks et al. |
| 2002/0058786 A1 | 5/2002 | Chivers et al. |
| 2002/0098567 A1 | 7/2002 | Vaidya et al. |
| 2003/0059840 A1 | 3/2003 | Chilkoti |
| 2003/0085228 A1 | 5/2003 | Oakes |
| 2003/0186293 A1 | 10/2003 | Ohnishi et al. |
| 2004/0009473 A1* | 1/2004 | Pease ................... 435/5 |
| 2004/0010163 A1 | 1/2004 | Hilbrig |
| 2004/0029143 A1 | 2/2004 | Van Ness et al. |
| 2004/0039177 A1 | 2/2004 | Yamanaka et al. |
| 2004/0058436 A1 | 3/2004 | Zhang et al. |
| 2004/0062140 A1 | 4/2004 | Cadogan et al. |
| 2004/0134846 A1 | 7/2004 | Akiyama et al. |
| 2004/0185437 A1* | 9/2004 | Hermet et al. .......... 435/5 |
| 2004/0219628 A1 | 11/2004 | Tashiro et al. ......... 435/34 |
| 2004/0248774 A1 | 12/2004 | Tayot |
| 2005/0016620 A1 | 1/2005 | Proulx et al. |
| 2005/0063259 A1 | 3/2005 | Isshiki et al. |
| 2005/0158782 A1 | 7/2005 | Furukawa et al. |
| 2005/0158851 A1 | 7/2005 | Furey |
| 2005/0175702 A1 | 8/2005 | Muller-Schulte |
| 2005/0224415 A1 | 10/2005 | Akiyama et al. |
| 2005/0238620 A1 | 10/2005 | Gomer et al. |
| 2005/0272146 A1 | 12/2005 | Hodge et al. |
| 2005/0282169 A1 | 12/2005 | Turner et al. |
| 2006/0118471 A1 | 6/2006 | Vidalinc |
| 2006/0121519 A1 | 6/2006 | Patchornik |
| 2006/0162882 A1 | 7/2006 | Ohara et al. |
| 2006/0189795 A1 | 8/2006 | Alstine et al. |
| 2006/0251610 A1 | 11/2006 | Nakahama |
| 2006/0257993 A1 | 11/2006 | McDevitt et al. |
| 2006/0270036 A1 | 11/2006 | Goodwin et al. |
| 2006/0281158 A1 | 12/2006 | Felder et al. |
| 2007/0148437 A1 | 6/2007 | Muller-Schulte |
| 2007/0193954 A1 | 8/2007 | Busson |
| 2007/0224241 A1 | 9/2007 | Stayton et al. |
| 2007/0249737 A1 | 10/2007 | Miller et al. |
| 2008/0032396 A1 | 2/2008 | Chokshi |
| 2008/0131957 A1 | 6/2008 | Ryan et al. |
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0254500 A1 | 10/2008 | Tashiro et al. |

(56) References Cited

U.S. PATENT DOCUMENTS

| | | |
|---|---|---|
| 2008/0255027 A1 | 10/2008 | Moya et al. |
| 2008/0284163 A1 | 11/2008 | Proulx et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0050566 A1 | 2/2009 | Kozlov et al. |
| 2009/0130704 A1 | 5/2009 | Gyure |
| 2009/0148961 A1 | 6/2009 | Luchini et al. |
| 2009/0155201 A1 | 6/2009 | Mandeville et al. |
| 2009/0181450 A1 | 7/2009 | Ribault et al. |
| 2009/0232737 A1 | 9/2009 | Moya et al. |
| 2009/0233327 A1 | 9/2009 | Lau et al. |
| 2009/0311776 A1 | 12/2009 | Kelly et al. |
| 2010/0012589 A1 | 1/2010 | Ribault et al. |
| 2010/0190963 A1 | 7/2010 | Moya et al. |
| 2010/0193148 A1 | 8/2010 | McKay et al. |
| 2010/0200507 A1 | 8/2010 | Kozlov et al. |
| 2010/0267933 A1 | 10/2010 | Wilson |
| 2010/0282425 A1 | 11/2010 | Karppi et al. |
| 2011/0020327 A1 | 1/2011 | Moya et al. |
| 2011/0065900 A1 | 3/2011 | Johansson et al. |
| 2011/0174735 A1 | 7/2011 | Ribault et al. |
| 2011/0257435 A1 | 10/2011 | Favero et al. |
| 2011/0313066 A1 | 12/2011 | Jaber et al. |
| 2012/0070836 A1 | 3/2012 | Zillmann et al. |
| 2012/0077249 A1 | 3/2012 | Ramaswamy et al. |
| 2012/0283419 A1 | 11/2012 | Thiyagarajan et al. |
| 2013/0005950 A1 | 1/2013 | Moya et al. |
| 2013/0123476 A1 | 5/2013 | Moya |
| 2013/0137860 A1 | 5/2013 | Moya et al. |
| 2013/0317204 A1 | 11/2013 | Moya et al. |
| 2014/0171594 A1 | 6/2014 | Jaber et al. |
| 2014/0263011 A1 | 9/2014 | Thiyagarajan et al. |
| 2015/0133636 A1 | 5/2015 | Xenopoulos et al. |
| 2015/0291656 A1 | 10/2015 | Hobel et al. |

FOREIGN PATENT DOCUMENTS

| | | |
|---|---|---|
| JP | 6-38732 A | 2/1994 |
| JP | 6-141890 A | 5/1994 |
| JP | 11-505714 A | 5/1999 |
| JP | 2000-507927 A | 6/2000 |
| JP | 2002-538430 A | 11/2002 |
| JP | 2003-114175 A | 4/2003 |
| JP | 2003-153684 A | 5/2003 |
| JP | 2006-284604 A | 10/2006 |
| JP | 2007-32559 A | 2/2007 |
| JP | 2008-519277 A | 6/2008 |
| KR | 10-2009-0113264 A | 10/2009 |
| WO | 91/00360 A1 | 1/1991 |
| WO | 92/20373 A1 | 11/1992 |
| WO | 93/04173 A1 | 3/1993 |
| WO | 93/16185 A2 | 3/1993 |
| WO | 93/08829 A1 | 5/1993 |
| WO | 93/14110 A1 | 7/1993 |
| WO | 93/16185 A2 | 8/1993 |
| WO | 94/15951 A1 | 7/1994 |
| WO | 95/06249 A1 | 3/1995 |
| WO | 95/19181 A1 | 7/1995 |
| WO | 95/23865 A1 | 9/1995 |
| WO | 96/02577 A1 | 2/1996 |
| WO | 96/27011 A1 | 9/1996 |
| WO | 96/30046 A1 | 10/1996 |
| WO | 96/37600 A1 | 11/1996 |
| WO | 96/40210 A1 | 12/1996 |
| WO | 97/26912 A2 | 7/1997 |
| WO | 98/06248 A2 | 2/1998 |
| WO | 98/23761 A1 | 6/1998 |
| WO | 98/33162 A1 | 7/1998 |
| WO | 98/45331 A2 | 10/1998 |
| WO | 98/51793 A1 | 11/1998 |
| WO | 99/01556 A2 | 1/1999 |
| WO | 00/12618 A1 | 3/2000 |
| WO | 00/46262 A1 | 8/2000 |
| WO | 00/67901 A1 | 11/2000 |
| WO | 00/75348 A1 | 12/2000 |
| WO | 01/07548 A1 | 2/2001 |
| WO | 01/40309 A2 | 6/2001 |
| WO | 2004/056312 A2 | 7/2004 |
| WO | 2004/092393 A1 | 10/2004 |
| WO | 2005/010141 A2 | 2/2005 |
| WO | 2005/021129 A1 | 3/2005 |
| WO | 2005/108546 A2 | 11/2005 |
| WO | 2005/118771 A2 | 12/2005 |
| WO | 2006/085321 A2 | 8/2006 |
| WO | 2006/138143 A1 | 12/2006 |
| WO | 2007/002690 A2 | 1/2007 |
| WO | 2007/038523 A2 | 4/2007 |
| WO | 2007/073311 A1 | 6/2007 |
| WO | 2007/104456 A | 9/2007 |
| WO | 2007/148230 A2 | 12/2007 |
| WO | 2008/004988 A1 | 1/2008 |
| WO | 2008/079280 A1 | 7/2008 |
| WO | 2008/079302 A2 | 7/2008 |
| WO | 2008/091740 A2 | 7/2008 |
| WO | 2008/097154 A1 | 8/2008 |
| WO | 2008/109667 A2 | 9/2008 |
| WO | 2009/089570 A1 | 7/2009 |
| WO | 2009/141664 A1 | 11/2009 |
| WO | 2009/158606 A2 | 12/2009 |
| WO | 2010/082894 A1 | 7/2010 |
| WO | 2014/123484 A1 | 8/2014 |
| WO | 2014/123485 A1 | 8/2014 |
| WO | 2014/133458 A1 | 9/2014 |
| WO | 2014/133459 A1 | 9/2014 |
| WO | 2014/133460 A1 | 9/2014 |

OTHER PUBLICATIONS

Office Action dated May 26, 2011 in co-pending U.S. Appl. No. 12/459,879.
Office Action mailed Feb. 4, 2014 in corresponding U.S. Appl. No. 12/383,131.
Final Rejection mailed Oct. 24, 2013 in corresponding U.S. Appl. No. 12/383,131.
Office Action mailed Jun. 11, 2013 in corresponding U.S. Appl. No. 12/383,131.
The Proceedings of the National Academy of Sciences, USA, vol. 90, No. 14, Jul. 1993, pp. 6444-6448, "'Diabodies': Small bivalent and bispecific antibody fragments", Holliger, et al.
Journal of Molecular Biology, vol. 227, No. 2, Sep. 1992, pp. 381-388, "By-passing Immunisation: Human Antibodies from Synthetic Repertoires of Germline VH Gene Segments Rearranged in vitro", Hoogenboom, et al.
Molecular Immunology, vol. 28, No. 9, Sep. 1991, pp. 1027-1037, "Construction and expression of antibody-tumor necrosis factor fusion proteins", Hoogenboom, et al.
Biotechnology and Bioengineering, vol. 60, No. 5, Dec. 1998, pp. 568-579, "Preparation of a New Thermo-Responsive Adsorbent with Maltose as a Ligand and Its Application to Affinity Precipitation", Hoshino, et al.
Transplantation, vol. 58, No. 3, 1994, pp. 377-380, "Administration of an anti-CD11a monoclonal antibody in recipients of kidney transplantation. A pilot study", Hourmant, et al.
Biotechnology Techniques, vol. 4, No. 1, 1990, pp. 55-60, "The Flocculation of Bacteria Using Cationic Synthetic Flocculants and Chitosan", Hughes, et al.
Bioseparation, vol. 7, No. 4-5, 1999, pp. 207-220, "Polycomplexes—potential for bioseparation", Izumrudov, et al.
Proc. Natl. Acad. Sci. USA, vol. 90, Mar. 1993, pp. 2551-2555, "Analysis of homozygous mutant chimeric mice: Deletion of the immunoglobulin heavy-chain joining region blocks B-cell development and antibody production", Jakobovits, et al.
Nature, vol. 362, Mar. 1993, pp. 255-258, "Germ-line transmission and expression of a human-derived yeast artificial chromosome", Jakobovits, et al.
Nature, vol. 321, May 1986, pp. 522-525, "Replacing the complementarity-determining regions in a human antibody with those from a mouse", Jones, et al.

(56) References Cited

OTHER PUBLICATIONS

Cancer Research (Suppl.), vol. 55, Dec. 1995, pp. 5908s-5910s, "Radiolabeled Anti-CD33 Monoclonal Antibody M195 for Myeloid Leukemias", Jurcic, et al.
Cancer Research (Suppl.), vol. 55, Dec. 1995, pp. 5899s-5907s, "Treatment of Non-Hodgkin's Lymphoma with Radiolabled Murine, Chimeric, or Humanized LL2, an Anti-CD22 Monoclonal Antibody", Juweid, et al.
Biotechnology and Bioengineering, vol. 40, No. 11, Dec. 1992, pp. 1381-1387, "Purification of Recombinant Protein A by Aqueous Two-Phase Extraction Integrated with Affinity Precipitation", Kamihira, et al.
Anal. Chem., vol. 69, No. 5, 1997, pp. 823-830, "Temperature-Responsive Liquid Chromatography. 2. Effects of Hydrophobic Groups in N-isopropylacrylamide Copolymer-modified Silica", Kanazawa, et al.
Journal of Chromatography A, vol. 1106, Feb. 2006, pp. 152-158, "Temperature-responsive stationary phase utilizing a polymer of proline derivative for hydrophobic interaction chromatography using an aqueous mobile phase", Kanazawa, et al.
Biomechanical Engineering Journal, vol. 40, No. 3, 2008, pp. 512-519, "Flocculation enhanced microfiltration of *Escherichia coli* lysate", Karim, et al.
Journal of Membrane Science, vol. 182, No. 1-2, Feb. 2001, pp. 161-172, "Flocculation to enhance microfiltration", Kim, et al.
Flocculation in Biotechnology and Separation Systems, 1987, pp. 429-439, "Removal of Cell and Cell Debris by Electrostatic Adsorption of Positively Charged Polymeric Particles", Kim, et al.
Growth Factors, vol. 7, 1992, pp. 53-64, "The Vascular Endothelial Growth Factor Proteins: Identification of Biologically Relevant Regions by Neutralizing Monoclonal Antibodies", Kim, et al.
The Journal of Immunology, pp. 2453-2455, Reprinted with permission from Nature, vol. 256 (5517): 495-497 (1975), "Continuous cultures of fused cells secreting antibody of predefined specificity", Kohler, et al.
The Journal of Immunology, vol. 148, No. 5, 1992, pp. 1547-1553, "Formation of a bispecific antibody by the use of leucine zippers", Kostelny, et al.
The Journal of Immunology, vol. 133, No. 6, 1984, pp. 3001-3005, "A human hybrid myeloma for production of human-monoclonal antibodies", Kozbor, et al.
Isolation and Purification of Proteins, 2003, edited by Rajni Hatti-Kaul, et al., pp. 237-275, "Precipitation of Proteins", Kumar, et al.
Biotechnology and Bioengineering, vol. 59, Issue 6, 1998, pp. 695-704, "Affinity Precipitation of Amylase Inhibitor from Wheat Meal by Metal Chelate Affinity Binding Using Cu(II)-Loaded Copolymers of 1-Vinylimidazole with N-Isopropylacrylamide", Kumar, et al.
Prog. Polym. Sci., vol. 32, 2007, pp. 1205-1237, "Smart polymers: Physical forms and bioengineering applications", Kumar, et al.
Biotechnology and Bioengineering, vol. 75, No. 5, Dec. 2001, pp. 570-580, "Type-Specific Separation of Animal Cells in Aqueous Two-Phase Systems Using Antibody Conjugates with Temperature-Sensitive Polymers", Kumar, et al.
Am Chem Society, ACS Symposium Series, vol. 362, Chapter 7, 1988, pp. 72-101, "Scale-Up of Bioseparations for Microbial and Biochemical Technology", Ladisch, et al.
Nature, vol. 227, No. 5259, Aug. 1970, pp. 680-685, "Cleavage of Structural Proteins during the Assembly of the Head of Bacteriophage T4", Laemmli.
Bioseparation, vol. 7, 1999, pp. 195-205, "Carboxymethyl cellulose as a new heterobifunctional ligand carrier for affinity precipitation of proteins", Lali, et al.
Journal of Biotechnology, vol. 49, No. 1-3, Aug. 1996, pp. 189-199, "Evaluation of affinity precipitation and a traditional affinity chromatographic precedure for purification of soybean lectin, from extracts of soya flour", Larsson, at al.
Journal of Pharmaceutical Sciences, vol. 100, No. 7, Jul. 2011, pp. 2551-2562, "Assessment of Net Charge and Protein-Protein Interactions of Different Monoclonal Antibodies", Lehermayr, et al.

AIChE Journal, vol. 55, No. 8, Aug. 2009, pp. 2070-2080, "Effect of Molecular Weight of Poly(N-isopropylacrylamide) Temperature-Sensitive Flocculants on Dewatering", Li, et al.
European Journal of Immunology, vol. 26, No. 1, Jan. 1996, pp. 1-9, "Antibody-targeted superantigen therapy induces tumor-infiltrating lymphocytes, excessive cytokine production, and apoptosis in human colon carcinoma", Litton, et al.
The Journal of Immunology, vol. 156, No. 4, 1996, pp. 1646-1653, "In Vivo Blockade of TNF-alpha by Intravenous Infusion of a Chimeric Monoclonal TNF-alpha Antibody in Patients with Rheumatoid Arthritis. Short Term Cellular and Molecular Effects", Lorenz, et al.
Journal of Chromatography B, vol. 878, No. 9-10, Mar. 2010, pp. 798-806, "Using precipitation by polyamines as an alternative to chromatographic separation in antibody purification processes", Ma, et al.
Innovative Food Science and Emerging Technologies, 2007, pp. 1-11, "Novel chromatographic separation—The potential of smart polymers", Maharjan, et al.
Analytical Chemistry, vol. 75, No. 13, Jul. 2003, pp. 2943-2949, "A Smart Microfluidic Affinity Chromatography Matrix Composed of Poly(N-isopropylacrylamide)-Coated Beads", Malmstadt, et al.
Bioconjugate Chem., 2003, vol. 14, No. 3, pp. 575-580, "Affinity Thermoprecipitation and Recovery of Biotinylated Biomolecules via a Mutant Streptavidin-Smart Polymer Conjugate", Malmstadt, et al.
Journal of Molecular Biology, vol. 222 No. 3, Dec. 1991, pp. 581-597, "By-passing Immunization—Human antibodies from V-gene Libraries Displayed on Phage", Marks, et al.
Bio/Technology, Nature Publishing Group, vol. 10, Jul. 1992, pp. 779-783, "By-Passing Immunization: Building High Affinity Human Antibodies by Chain Shuffling", Marks, et al.
Nature, vol. 348, Dec. 1990, pp. 552-554, "Phage antibodies: filamentous phage displaying antibody variable lomains", McCafferty, et al.
Merriam Webster Dictionary, accessed May 14, 2013 at http://www.merriam-webster.com/dictionary/associated, Definition of the word "associate . . . " 6 pages.
Millipore Pure Science Laboratory Catalogue 1999/2000, Ultrafiltration Discs and Stirred Cells, p. 127, "Solvent-resistant Stirred Cells" and "High-Output Stirred Cells", 3 pages.
Nature, vol. 305, Oct. 1983, pp. 537-540, "Hybrid hybridomas and their use in immunohistochemistry", Milstein, et al.
Journal of Biochemical and Biophysical Methods, vol. 24, 1992, pp. 107-117, "Single-step purification of F(ab')sub.2 fragments of mouse monoclonal antibodies (immunoglobulins G1) by hydrophobic interaction high performance liquid chromatography using TSKgel Phenyl-5PW", Morimoto, et al.
Proc. Natl. Acad. Sci. USA, vol. 81, Nov. 1984, pp. 6851-6855, "Chimeric human antibody molecules: Mouse antigen-binding domains with human constant region domains", Morrison, et al.
American Inst. of Chem. Engineers, Biotechnology Progress, V 26, No. 5, (2010), pp. 1322-1331, "Monoclonal Antibody Purification Using Cationic Polyelectrolytes: An Alternative to Column Chromatography", Peram, et al.
Flocculation in Biotechnology and Separation Systems, 1987, pp. 457-466, "Flocculation of Cell Debris for Improved Separation by Centrifugation", Persson, et al.
The Journal of Immunology, vol. 151, No. 5, Sep. 1993, pp. 2623-2632, "Humanization of an Antibody Directed Against IgE", Presta, et al.
Current Opinion in Structural Biology, vol. 2, No. 4, Aug. 1992, pp. 593-596, "Antibody Engineering", Presta.
Protein Expression and Purification, vol. 7, Article No. 0042, 1996, pp. 294-298, "Sequential Precipitation with Reversibly Soluble Insoluble Polymers as a Bioseparation Strategy: Purification of B-Glucosidase from Trichoderma ongibrachiatum", Agarwal, et al.
Science, vol. 229, Jul. 1985, pp. 81-83, "Preparation of Bispecific Antibodies by Chemical Recombination of Monoclonal Immunoglobulin G1 Fragments", Brennan, et al.
Macromolecular Bioscience, vol. 5, No. 5, 2005, pp. 373-378, "Highly Branched Stimuli Responsive Poly[(N-isopropylacrylamide)-co-(1,2-propandiol-3-methacrylate)]s with Protein Binding Functionality", Carter, et al.

(56) References Cited

OTHER PUBLICATIONS

Cancer Research (Suppl.), vol. 55, Dec. 1, 1995, pp. 5852s-5856s, "Biological Activity of Two Humanized Antibodies against Two Different Breast Cancer Antigens and Comparison to Their Original Murine Forms", Ceriani, at al.
Bioseperation, vol. 7, No. 4-5, Jul. 1999, pp. 231-240, "Affinity precipitation of monoclonal antibodies by nonstoichiometric polyelelectrolyte complexes", Dainiak, et al.
Biotechnology and Bioengineering, vol. 79, No. 3, Aug. 5, 2002, pp. 271-276, "Affinity Separation Using an Fv Antibody Fragment-"Smart" Polymer Conjugate", Fong, et al.
Trends in Biotechnology, vol. 9, No. 6, Jun. 1991, pp. 191-196, "Application of reversibly soluble polymers in bioprocessing", Fuji!, et al.
Bioseparation, vol. 5, 1995, pp. 339-350, "Alternative modes of precipitation of Eudragit S-100: a potential ligand carrier for affinity precipitation of protein", Guoqiang, et al.
Am Inst. of Chem Engineers Journal, Jul. 2003, vol. 49, No. 7, pp. 1687-1701, "Flocculation of Biological Cells: Experiment vs. Theory", Han, et al.
Journal of Chromatography B, vol. 790, Jun. 2003, pp. 79-90, "Protein purification by affinity precipitation", Hilbrig, al.
Cancer Research (Suppl.), vol. 55, Dec. 1995, pp. 5916s-5920s, "Radioimmunotherapy for Breast Cancer Using Escalating Fractionated Doses of 131-I-labeled Chimeric L6 Antibody with Peripheral Blood Progenitor Cell Transfusions", Richman, et al.
Nature, vol. 332, Mar. 1988, pp. 323-327, "Reshaping human antibodies for therapy", Riechmann, et al.
Journal of Biotechnology, vol. 128, No. 4, Mar. 2007, pp. 813-823, "The use of chitosan as a flocculant in mammalian cell culture dramatically improves clarification throughput without adversely impacting monoclonal antibody recovery", Riske, et al.
Biotechnol. Prog, vol. 24, No. 3, May/Jun. 2008, pp. 488-495, "Advances in Primary Recovery: Centrifugation and Membrane Technology", Roush, et al.
Anal. Chem., vol. 71, No. 20, Oct. 1999, pp. 4506-4512, "Concentration of Hydrophobic Organic Compounds by Polymer-Mediated Extraction", Saitoh, et al.
Kona, No. 20, 2002, pp. 246-250, "Flocculation Mechanism of Suspended Particles Using the Hydrophilic/Hydrophobic Transition of a Thermosensitive Polymer", Sakohara, et al.
Advanced Drug Delivery Reviews, vol. 58, No. 15, 2006, pp. 1655-1670, "Thermo-and pH-responsive polymers in drug delivery", Schmaljohann.
The Journal of Physical Chemistry B, vol. 111, No. 29, 2007, pp. 8649-8654, "Cationic Flocculants Carrying Hydrophobic Functionalities: Applications for Solid/Liquid Separation", Schwarz, et al.
Biotechnology and Bioengineering, vol. 34, No. 3, 1989, pp. 387-393, "Purification of Wheat Germ Agglutinin Using Affinity Flocculation with Chitosan and a Subsequent Centrifugation or Flotation Step", Senstad, et al.
Journal of the Chemical Society of Japan, No. 8, Aug. 1991, pp. 1115-1126 (English Abstract Submitted), "Structure and Hydrolysis Activity of Poly(alylamine)s having Hydrophobic Groups", Seo, et al.
Macromolecules, American Chemical Society, vol. 24, No. 15, 1991, pp. 4255-4263, "Self-organization of Poly (allylamine)s Containing Hydrophobic Groups and Its Effect on the Interaction with Small Molecules. 1. Static Fluorometry", Seo, et al.
J. Exp. Med., vol. 175, 1992, pp. 217-225, "Development of Humanized Bispecific Antibodies Reactive with Cytotoxic Lymphocytes and Tumor Cells Overexpressing the HER2 Protooncogene", Shalaby, et al.
Journal of Biotechnology, vol. 49, 1996, pp. 173-178, " Flocculation of cell, cell debris and soluble protein with methacryloyloxyethyl trimethylammonium chloride-acrylonitrile copolymer", Shan, et al.
Cancer Research (Suppl.), vol. 55, Dec. 1995, pp. 5935s-5945s, "Evaluation of a Complementarity-Determining Region-Grafted (Humanized) Anti-Carcinoembryonic Antigen Monoclonal Antibody in Preclinical and Clinical Studies", Sharkey, et al.
The Journal of Immunology, vol. 151, No. 4, 1993, pp. 2296-2308, "A Humanized CD18 Antibody Can Block Function Without Cell Destruction", Sims, et al.
Chest, vol. 103, No. 3, Mar. 1993, pp. 932-943, "Immunologic Therapy for ARDS, Septic Shock, and Multiple-Organ Failure", St. John, et al.
Cell, vol. 66, No. 6, 1991, pp. 1133-1144, "The B Lymphocyte Adhesion Molecule CD22 Interacts with Leukocyte Common Antigen CD45RO on T Cells and a2-6 Sialyltransferase, CD75, on B Cells", Stamenkovic, et al.
The Affinity Precipitation for the Isolation of Biomolecules, No. 3862, Aug. 2007, pp. 1-130, 146 pages, Stocker-Majd, et al, submitted in two parts.
Transplant International, vol. 4, No. 1, 1991, pp. 3-7, "Anti-LFA1 monoclonal antibody (25.3) for treatment of steroid-resistant grade III-IV acute graft-versus-host disease", Stoppa, et al.
Journal of Chromatography A, vol. 1114, 2006, pp. 239-249, "Temperature sensitive dopamine-imprinted (N,N-methylene-bis-acrylamide cross-linked) polymer and its potential application to the selective extraction of adrenergic drugs from urine", Suedee, et al.
Analytical Sciences, vol. 3, No. 6, Dec. 1987, pp. 479-488, "Ion Association Reagents, A Review", Toei.
The EMBO Journal, vol. 10, No. 12, 1991, pp. 3655-3659, "Bispecific single chain molecules (Janusins) target cytotoxic lymphocytes on HIV infected cells", Traunecker, et al.
The Journal of Immunology, vol. 147, No. 1, Jul. 1991, pp. 60-69, "Trispecific F(ab')3 derivatives that use cooperative signaling via the TCR/CD3 complex and CD2 to activate and redirect resting cytotoxic T cells", Tutt, et al.
Flocculation in Biotechnology and Separation Systems, 1987, pp. 351-368, "Aspects of Bioflocculation: An Overview", Unz.
Nature Biotechnology, vol. 14, 1996, pp. 309-314, "Human Antibodies with Sub-nanomolar Affinities Isolated from a Large Non-immunized Phage Display Library", Vaughan, et al.
Science, vol. 239, Mar. 1988, pp. 1534-1536, "Reshaping Human Antibodies: Grafting an Antilysozyme Activity", Verhoeyen, et al.
Nucleic Acids Research, vol. 21, No. 9, 1993, pp. 2265-2266, "Combinatorial infection and in vivo recombination: a strategy for making large phage antibody repertoires", Waterhouse, et al.
Biotechnology and Bioengineering, vol. 108, No. 1, Jan. 2011, pp. 50-58, "Effects of Solution Environment on Mammalian Cell Fermentation Broth Properties: Enhanced Impurity Removal and Clarification Performance", Westoby, et al.
Biotechnology and Bioengineering, vol. 86, No. 6, 2004, pp. 612-621, "Clearance of Minute Virus of Mice by Flocculation and Microfiltration", Wickramasinghe, et al.
Desalination, vol. 147, No. 1-3, 2002, pp. 25-30, "Enhanced microfiltration of yeast by flocculation", Wickramasinghe, et al.
Separation Science and Technology, vol. 37, No. 1, pp. 217-228, 2002, "Selective Precipitation of Water-Soluble Separation Using Designed Polyelectrolyte", Yu, et al.
Protein Engineering, vol. 8, No. 10, 1995, pp. 1057-1062, "Engineering linear F(ab')2 fragments for efficient production in *Escherichia coli* and enhanced antiproliferative activity", Zapata, et al.
Nucleic Acids Research, vol. 31, No. 13, 2003, pp. 3406-3415, "Mfold web server for nucleic acid folding and hybridization prediction", Zuker.
International Search Report mailed Mar. 31, 2008 in co-pending PCT application No. PCT/US2007/26040.
International Search Report dated Apr. 24, 2008 in co-pending PCT application No. PCT/US2007/26090.
International Search Report dated Aug. 27, 2009 in co-pending PCT application No. PCT/US2008/013736.
Extended European Search Report mailed Nov. 17, 2009 in co-pending EP Patent Application No. 09161982.5, 6 pages.
International Search Report/Written Opinion mailed Nov. 12, 2009 in co-pending PCT Patent Application No. PCT/US2009/002787, 9 pages.

(56) References Cited

OTHER PUBLICATIONS

International Preliminary Report on Patentability/Written Opinion issued Dec. 13, 2010 in co-pending PCT Patent Application No. PCT/US2009/002787, 6 pages.
International Search Report dated Feb. 18, 2010 in co-pending PCT application No. PCT/US2009/006363.
International Preliminary Report on Patentability mailed Jun. 30, 2011 in co-pending PCT application No. PCT/ US2009/006363.
International Search Report and Written opinion dated Jan. 29, 2010 in co-pending PCT application No. PCT/US09/67097, 8 pages.
International Preliminary Report on Patentability/Written Opinion mailed Jun. 30, 2011 in co-pending PCT Patent Application No. PCT/US2009/067097, 7 pages.
Japanese Communication mailed Oct. 16, 2012 in co-pending Japanese patent application No. 2011-542238.
Japanese communication, with English translation, dispatched Sep. 2, 2014 in co-pending Japanese patent application No. 2013-083213.
European Search Report mailed Jul. 9, 2013 in co-pending European Patent Application No. EP 09835506.8.
International Search Report/Written Opinion dated Dec. 6, 2011 in co-pending PCT application No. PCT/US2011/039595.
International Preliminary Report on Patentability mailed Dec. 20, 2012 in co-pending PCT application No. PCT/US2011/039595.
International Search Report dated Oct. 31, 2011 in co-pending PCT application No. PCT/US2011/036648.
International Preliminary Report on Patentability mailed Nov. 29, 2012 in co-pending PCT application No. PCT/US2011/036648.
Office Action-Restriction-mailed Feb. 7, 2012 in co-pending U.S. Appl. No. 12/448,004.
Office Action mailed Jul. 26, 2012 in co-pending U.S. Appl. No. 12/448,004.
Office Action-Restriction-mailed Sep. 30, 2014 in co-pending U.S. Appl. No. 13/732,613.
Office Action mailed Mar. 16, 2015 in co-pending U.S. Appl. No. 13/732,613.
Final rejection mailed Oct. 20, 2015 in co-pending U.S. Appl. No. 13/732,613.
Office action mailed May 9, 2013 in co-pending U.S. Appl. No. 13/747,495.
Office Action mailed Nov. 25, 2013 in co-pending U.S. Appl. No. 13/747,495.
Final Rejection mailed Aug. 8, 2014 in co-pending U.S. Appl. No. 13/747,495.
Office action mailed Sep. 17, 2015 in co-pending U.S. Appl. No. 13/747,495.
Office Action—Restriction—mailed Oct. 28, 2013 in co-pending U.S. Appl. No. 13/955,024.
Office Action mailed Dec. 9, 2013 in co-pending U.S. Appl. No. 13/955,024.
Notice of Allowance mailed Aug. 4, 2014 in co-pending U.S. Appl. No. 13/955,024.
Notice of Allowance mailed Sep. 4, 2015 in co-pending U.S. Appl. No. 13/955,024.
Notice of Allowance mailed Nov. 6, 2015 in co-pending U.S. Appl. No. 13/955,024.
Office Action-Restriction-mailed Apr. 27, 2012 in co-pending U.S. Appl. No. 12/592,744.
Office Action-Restriction-mailed Jul. 17, 2012 in co-pending U.S. Appl. No. 12/633,141.
Office Action mailed Jan. 31, 2013 in co-pending U.S. Appl. No. 12/633,141.
Final Rejection mailed Jun. 25, 2013 in co-pending U.S. Appl. No. 12/633,141.
Office Action mailed Apr. 3, 2014 in co-pending U.S. Appl. No. 12/633,141.
Final Rejection mailed Aug. 14, 2014 in co-pending U.S. Appl. No. 12/633,141.
Office Action mailed Mar. 2, 2015 in co-pending U.S. Appl. No. 12/633,141.
Final Rejection mailed Jul. 27, 2015 in co-pending U.S. Appl. No. 12/633,141.
Final Rejection mailed Feb. 25, 2016 in co-pending U.S. Appl. No. 12/633,141.
Office Action mailed Feb. 22, 2013 in co-pending U.S. Appl. No. 13/610,954.
Notice of Allowance mailed Oct. 31, 2013 in co-pending U.S. Appl. No. 13/610,954.
Notice of Allowance mailed Nov. 14, 2014 in co-pending U.S. Appl. No. 13/610,954.
Notice of Allowance mailed Oct. 20, 2015 in co-pending U.S. Appl. No. 13/610,954.
Office Action-Restriction-mailed Nov. 21, 2012 in co-pending U.S. Appl. No. 13/155,912.
Office Action mailed Apr. 30, 2013 in co-pending U.S. Appl. No. 13/155,912.
Notice of Allowance mailed Mar. 2, 2016 in co-pending U.S. Appl. No. 13/747,495.
Protein Expression and Purification, vol. 7, Article No. 0042, 1996, pp. 294-298, "Sequential Precipitation with Reversibly Soluble Insoluble Polymers as a Bioseparation Strategy: Purification of B-Glucosidase from Trichoderma Iongibrachiatum", Agarwal, et al.
Journal of Chromatography B, vol. 761, No. 2, 2001, pp. 247-254, "New antibody purification procedure using a thermally responsive poly(N-isopropylacrylamide)-dextran derivative conjugate", Anastase-Ravion, et al.
Cell, vol. 61, No. 7, Jun. 1990, pp. 1303-1313, "CD44 is the Principal Cell Surface Receptor for Hyaluronate", Aruffo, et al.
Process Technology Proceedings, vol. 4, Proceedings of the International Symposium on Flocculation in Biotechnology and Separations Systems, San Francisco, California, Jul. 28-Aug. 1, 1986, pp. 429 & 441, "Flocculation in Biotechnology and Separation Systems", Attia.
Journal of Chromatography A, Vol. 1119, 2006, pp. 58-65, "Aqueous chromatography system using pH- and temperature-responsive stationary phase with ion-exchange groups", Ayano, et al.
Science, vol. 229, Jul. 1985, pp. 81-83, "Preparation of Bispecifc Antibodies by Chemical Recombination of Monoclonal Immunoglobulin G1 Fragments", Brennan, et al.
Monoclonal Antibody Production Techniques and Application, pp. 51-63 (Marcel Dekker, Inc., New York 1987), "Mouse-Human Myeloma Partners for the Production of Heterohybridomas", Brodeur, et al.
The Year in Immunology, vol. 7, 1993, pp. 33-40, "Designer Mice: The Production of Human Antibody Repertoires in Transgenic Animals", Bruggemann, et al.
Bio/Technology, Nature Publishing Group, vol. 10, Feb. 1992, pp. 163-167, "High Level *Escherichia coli* Expression and Production of a Bivalent Humanized Antibody Fragment", Carter, et al.
Macromolecular Bioscience, vol. 5, No. 5, 2005, pp. 373-378, "Highly Branched Stimuli Responsive Poly[(N-Isopropylacrylamide)-co-(1,2-propandiol-3-methacrylate)]s with Protein Binding Functionality", Carter, et al.
Proc. Natl. Acad. Sci. USA, vol. 89, May 1992, pp. 4285-4289, "Humanization of an anti-p185HER2 antibody for human cancer therapy", Carter, et al.
"Technology: Temperature-responsive polymers", document retrieved on Oct. 13, 2010, available at: http://www.cellseed.com/technology-e/index.html, 1 page, Cellseed, Inc.
Cancer Research (Suppl.), vol. 55, Dec. 1, 1995, pp. 5852s-5856s, "Biological Activity of Two Humanized Antibodies against Two Different Breast Cancer Antigens and Comparison to Their Original Murine Forms", Ceriani, et al.
Macromolecular Chemistry and Physics, vol. 196, No. 4, Apr. 1995, pp. 1251-1259, "A new temperature- and pH-responsive copolymer for possible use in protein conjugation", Chen, et al.
Nature, vol. 373, No. 5, Jan. 1995, pp. 49-52, "Graft copolymers that exhibit temperature-induced phase transitions over a wide range of pH", Chen, et al.
Langmuir, vol. 21, No. 25, 2005, pp. 11673-11677, "pH-Dependence of the Properties of Hydrophobically Modified Polyvinylamine", Chen, et al.

(56) References Cited

OTHER PUBLICATIONS

Biomaterials, vol. 11, No. 9, Nov. 1990, pp. 631-633, "Polymer-protein conjugates. II. Affinity precipitation separation of human immunogammaglobulin by a poly (N-isopropylacrylamide)-protein A conjugate", Chen, et al.
Colloids and Surfaces B: Biointerfaces, vol. 6, 1996, pp. 37-49, "Characterization of pH-sensitive polymeric supports for selective precipitation of proteins", Chern, et al.
Journal of Molecular Biology, vol. 196, 1987, pp. 901-917, "Canonical Structures for the Hypervariable Regions of Immunoglobulins", Chothia, et al.
Arthritis & Rheumatism, vol. 39, No. 1, Jan. 1996, pp. 52-56, "Percentage of anti-CD4 monoclonal antibody-coated lymphocytes in the rheumatoid joint is associated with clinical improvement. Implications for the development of immunotherapeutic dosing regimens", Choy, et al.
Nature, vol. 352, Aug. 1991, pp. 624-628, "Making antibody fragments using phage display libraries", Clackson, et al.
Bioseparation, vol. 7, No. 4-5, Jul. 1999, pp. 231-240, "Affinity precipitation of monoclonal antibodies by nonstoichiometric polyelelectrolyte complexes", Dainiak, et al.
Journal of Colloid and Interface Science, vol. 179, No. 1, 1996, pp. 188-193, "Temperature-Sensitive Flocculants Based on Poly (N-isopropylacrylamide-co-diallyldimethylammonium Chloride)", Deng, et al.
Critical Care Medicine, vol. 23, No. 9, Sep. 1995, pp. 1461-1469, "CDP571, a humanized antibody to human tumor necrosis factor-alpha: Safety, pharmacokinetics, immune response, and influence of the antibody on cytokine concentrations in patients with septic shock", Dhainaut, et al.
Nature, vol. 411, May 2001, pp. 59-62, "Size-dependent control of the binding of biotinylated proteins to streptavidin using a polymer shield", Ding, et al.
Nature, vol. 355, Jan. 1992, pp. 258-262, "Immunization of hu-PBL-SCID mice and the rescue of human monoclonal Fab fragments through combinatorial libraries", Duchosal, et al.
Journal of Polymer Science, vol. XIII, No. 6, Feb. 1954, pp. 85-91, "Viscosities of Dilute Aqueous Solutions of a Partially Quaternized Poly-4-vinylpyridine at Low Gradients of Flow", Eisenberg, et al.
The Journal of Immunology, vol. 155, No. 2, 1995, pp. 925-937, "Engineered Anti-CD38 Monoclonal Antibodies for Immunotherapy of Multiple Myeloma", Ellis, et al.
Flocculation in Biotechnology and Separation Systems, 1987, pp. 441-455, "Flocculation of *E. Coli* Bacteria With Cationic Polyelectrolytes", Eriksson, et al.
Flocculation in Biotechnology and Separation Systems, 1987, pp. 383-398, "Genetic Control of Flocculation of Yeast With Respect to Application in Biotechnology", Esser, et al.
Journal of Chromatography A, vol. 1195, 2008, pp. 94-100, "Purification of human immunoglobulin G by thermoseparating aqueous two-phase systems", Ferriera, et al.
Biotechnology and Bioengineering, vol. 79, No. 3, Aug. 5, 2002, pp. 271-276, "Affinity Separation Using an Fv Antibody Fragment—"Smart" Polymer Conjugate", Fong, et al.

Bioconjugate Chem., vol. 10, No. 5, 1999, pp. 720-725, "Thermoprecipitation of Steptavidin via Oligonucleotide-Mediated Self-Assembly with Poly (N-isopropylacrylamide)", Fong, et al.
Chimia 55, No. 3, 2001, pp. 196-200, "Stimulus-Responsive Polymers for Bioseparation", Freitag, et al.
Trends in Biotechnology, vol. 9, No. 6, Jun. 1991, pp. 191-196, "Application of reversibly soluble polymers in bioprocessing", Fujii, et al.
Trends in Biotechnology, vol. 17, No. 8, Aug. 1999, pp. 335-340, "'Smart' polymers and what they could do in biotechnology and medicine", Galaev, et al.
Russian Chemical Reviews, vol. 64, No. 5, 1995, pp. 471-489, "'Smart' polymers in biotechnology and medicine", Galaev.
Journal of Chromatography A, vol. 684, 1994, pp. 45-54, "Interaction of Cibacron Blue with polymers: implications for polymer-shielded dye-affinity chromatography of phosphofructokinase from baker's yeast", Galaev, et al.
Biotechnology and Bioengineering, vol. 71, No. 3, 2000/2001, pp. 223-234, "Use of the Avidin (Imino)biotin System as a General Approach to Affinity Precipitation", Garret-Flaudy, et al.
Process Biochemistry, vol. 34, No. 6-7, Sep. 1999, pp. 577-580, "Purification of Aspergillus sp xylanase by precipitation with an anionic polymer Eudragit S 100", Gawande, et al.
Biotechnol. Appl. Biochem. (1999), vol. 30, pp. 235-244, "Expression system for foreign genes using the fission yeast Schizosaccharomyces pombe", Giga-Hama, et al.
Progress in Polymer Science, vol. 29, No. 12, Dec. 2004, pp. 1173-1222, "Stimuli-responsive polymers and their bioconjugates", Gil, et al.
Monoclonal Antibodies: Principles and Practice, Academic Press, 1986, pp. 59-103, "3. Production of Monoclonal Antibodies", Goding.
The Journal of Immunology, vol. 155, No. 10, 1995, pp. 4996-5002, "Construction and Characterization of a Humanized Anti-gamma-Ig Receptor Type I (Fc gamma RI) Monoclonal Antibody", Graziano, et al.
The Journal of Immunology, vol. 152, No. 11, 1994, pp. 5368-5374, "Efficient Tumor Cell Lysis Mediated by a Bispecific Single Chain Antibody Expressed in *Escherichia coli*", Gruber, et al.
Bioseparation, vol. 5, 1995, pp. 339-350, "Alternative modes of precipitation of Eudragit S-100: a potential ligand aarrier for affinity precipitation of protein", Guoqiang, et al.
Journal of Molecular Recognition, vol. 9, 1996, pp. 356-359, XP-002538983, "Affinity Precipitation of Proteins", Gupta, et al.
Am Inst. of Chem Engineers Journal, Jul. 2003, vol. 49, No. 7, pp. 1687—1701, "Flocculation of Biological Cells: Experiment vs. Theory", Han, et al.
Analyst, vol. 129, 2004, pp. 421-427, "Capturing of acidic macromolecules from biological samples using a temperature-responsive polymer modified with poly-L-lysine", Hayashi, et al.
Journal of Chromatography B, vol. 790, Jun. 2003, pp. 79-90, "Protein purification by affinity precipitation", Hilbrig, at al.

* cited by examiner

METHOD AND UNIT FOR PREPARING A SAMPLE FOR THE MICROBIOLOGICAL ANALYSIS OF A LIQUID

BACKGROUND OF THE INVENTION

The present invention concerns the preparation of a sample for the microbiological analysis of a liquid.

It is known that there are liquids which may contain different types of microorganisms, among which the microbiological analysis must only concern one or several types.

These liquids exist for example at the end of a manufacturing chain for monoclonal antibodies. More particularly, such liquids, bearing eukaryotes which have enabled the antibodies to be produced, may possibly be contaminated with bacteria and/or viruses.

The presence of the eukaryote cells may hinder the microbiological analysis of the bacteria and viruses either by liberating toxins which may adversely affect the growth of the microorganisms in the case of conventional detection on a gel growth medium (detection of false negatives) or by perturbing the reading of the results in the case of fast detection (detection of false positives) by luminescence, fluorescence, by amplification or hybridization or by any other method of analysis of the nucleic acids of those microorganisms.

In order to carry out a reliable analysis of this type of liquid, it is thus appropriate to prepare a sample in which selection has been made of only the microorganisms (the bacteria and/or viruses in the example given above) belonging to the types of microorganisms which it is desired to detect.

Methods are already known for preparing a sample for the analysis of a liquid in which the microorganisms to detect are selected by exploiting the differences in morphological characteristics (physical and/or chemical) between the different types of microorganisms.

More particularly, a method of preparation is already known comprising a step of selection consisting of adding into the liquid to analyze a reagent adapted to carry out a specific lysis of the microorganisms belonging to the types of microorganisms which it is not desired to keep in the sample, then of filtering the liquid on a membrane so as to collect on that membrane a sample containing solely the microorganisms to detect and which have not reacted specifically with the lysing agent (those having undergone the lysis being destroyed and having passed through the membrane). The sample so collected is then retrieved to be analyzed with conventional or fast microbiological analysis techniques.

Another solution also for forming the sample consists of separating the microorganisms to keep from the others by virtue of their differences in mass by centrifuging at low speed.

SUMMARY OF THE INVENTION

The invention concerns preparing a sample according to a similar method while at the same time having improved performance and being simpler and more convenient to implement.

To that end it provides a method of preparing a sample for the microbiological analysis of a liquid which may contain microorganisms of several different types each having predetermined morphological characteristics, which method comprises the step of making a selection of the microorganisms from said different types of microorganisms, characterized in that said step of making a selection comprises:

the step of procuring a unit for preparing said sample comprising a generally tubular body within which are fixed a first and a second membrane, said body having an opening for introduction of said liquid, a first compartment between said introduction opening and said first membrane, a second compartment between said first and second membranes and a third compartment on the opposite side of said second membrane from said first membrane, said first membrane having a predetermined first pore diameter and said second membrane a predetermined second pore diameter less than said predetermined first pore diameter of said first membrane;

the step of passing a predetermined volume of said liquid from the first to the second compartment through said first membrane;

the step of passing all the filtrate, having so reached the second compartment, from the second to the third compartment through said second membrane in order to collect said sample on said second membrane with said microorganisms selected from said different types of microorganisms which are those of which the size is less than the predetermined pore diameter of said first membrane and greater than the predetermined pore diameter of said second membrane; and the step of retrieving said sample so collected on said second membrane.

In the method according to the invention, the sample formed of the microorganisms to analyze (bacteria and/or viruses for example) is collected on the second membrane after having been separated from the undesired microorganisms (for example eukaryote cells) of too great a size to pass through the first membrane.

Such a selection of the microorganisms on the basis of their differences in size is particularly effective, often more so than in the aforementioned methods of the prior art.

An explanation of this appears to be that, in the case of centrifuging, a portion of the microorganisms to collect is taken by centrifugal force with the microorganisms to eliminate; and, in the case of chemical lysis, that the lysing agent is never perfectly selective such that a small but non-zero proportion of the microorganisms to collect undergoes lysis and is thus not collected on the membrane, whereas in the method according to the invention (selection by size), such marginal effects are negligible, or even non-existent.

According to preferred features, for reasons of simplicity and convenience with regard both to manufacture and to use:

the step of procuring a preparation unit comprises the step of selecting a preparation unit of which the body comprises a first portion to which is fixed said first membrane and a second portion to which is fixed said second membrane, said portions being detachable from each other, and the step of retrieving said sample comprises the step of detaching said second portion of said body from said first portion of said body; and/or the step of procuring a preparation unit comprises the step of selecting a preparation unit in the body of which is formed an auxiliary opening capable of being unstopped communicating with said second compartment and the step of retrieving said sample comprises the step of unstopping said opening, the step of depositing an agent for lysing said microorganisms selected on said second membrane by said auxiliary opening then the step of passing the lysate so formed from the second to the third compartment through said second membrane.

It is thus possible, either by virtue of a body formed in two detachable portions, or by virtue of an aperture provided in that body, to have access to the second membrane and more particularly to the face of the second membrane on which the sample has been collected.

According to other preferred features, for the same reasons as those stated above:

the steps of passing said liquid through said membranes are performed by placing said third compartment under reduced pressure;

the steps of passing said liquid through said membranes are performed by placing said first compartment under increased pressure;

the steps of passing said liquid through said membranes are performed by centrifuging said preparation unit;

the step of procuring a preparation unit comprises the step of selecting as said first membrane a membrane of pore diameter greater than 1 µm;

the step of procuring a preparation unit comprises the step of selecting as said second membrane a membrane of pore diameter less than 0.65 µm; and/or the step of procuring a preparation unit comprises the step of selecting as said second membrane a membrane of pore diameter less than 0.1 µm;

According to a second aspect, the invention also concerns a unit for preparing a sample suitable for the implementation of the method as set forth above, characterized in that it comprises a generally tubular body within which are fixed a first and a second membrane, said body having an opening for introduction of said liquid, a first compartment between said introduction opening and said first membrane, a second compartment between said first and second membranes and a third compartment on the opposite side of said second membrane from said first membrane, said first membrane having a predetermined first pore diameter and said second membrane a predetermined second pore diameter less than said predetermined first pore diameter of said first membrane, said unit being adapted to pass a predetermined volume of said liquid from the first to the second compartment by said first membrane then to pass all the filtrate, having so reached the second compartment, from the second to the third compartment through said second membrane in order to collect said sample on said second membrane; said body also comprising means for retrieving said sample so collected on said second membrane.

The preparation unit is thus designed to make it possible to pass the entirety of the predetermined volume through the two membranes (with the exception of course of the parts retained by the membranes), and furthermore, to have access to the sample by virtue of the means for retrieving the sample.

It will be noted that a simple filtering unit with several stages, for example a solution clarification unit, would not be able to serve as a preparation unit according to the invention, since such a filtering unit is not made with membranes, would not be adapted to pass all the filtrate arriving in an intermediate compartment through the second stage (a residual filtrate would always remain) and/or would lack means for retrieving the sample.

According to preferred features, for reasons of simplicity and convenience with regard both to manufacture and to use, said first membrane is permeable to the air when wet.

In this manner, when the liquid has been entirely emptied from the first compartment and the first membrane comes into contact with the air on the side which is turned towards that compartment, that membrane, by virtue of the sufficient size of its pores, remains permeable to the air (no bubble point phenomenon) such that the air may penetrate by that membrane into the second compartment to enable the liquid which it contains to be evacuated.

According to other preferred features, for the same reasons as those stated above:

the pores of said first membrane are of diameter greater than 1 µm;

the pores of said second membrane are of diameter less than 0.65 µm;

the pores of said second membrane are of diameter less than 0.1 µm;

said body comprises a first portion to which is fixed said first membrane and a second portion to which is fixed said second membrane and said retrieval means are means for detachment of said second portion from said first portion;

said retrieval means comprise an opening capable of being unstopped formed in said body and communicating with said second compartment;

said body comprises a cup delimiting said third compartment; and/or said cup is detachable.

BRIEF DESCRIPTION OF THE DRAWINGS

The features and advantages of the invention will appear from the following description, given by way of preferred but non-limiting example, with reference to the accompanying drawings in which.

DETAILED DESCRIPTION OF THE INVENTION

Figure 1:
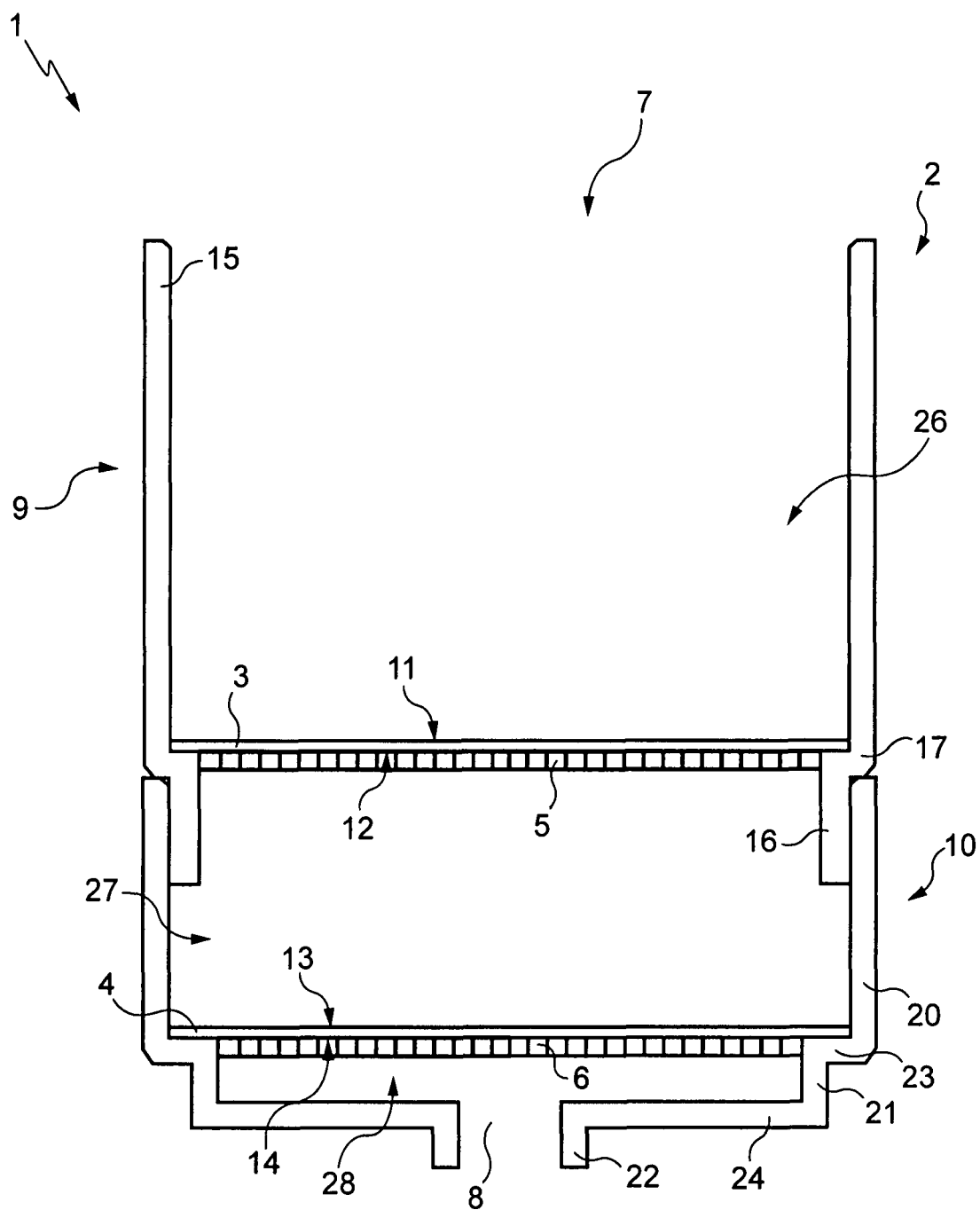
FIG. 1 is a cross-section view of a preparation unit according to the invention.

The preparation unit 1 illustrated in FIG. 1 comprises a generally tubular body 2 within which are fixed a membrane 3, a membrane 4 and two porous supports 5 and 6.

The membranes 3 and 4 are of polyvinylidene fluoride (PVDF), the membrane 3 having pores of diameter equal to 5 µm and the membrane 4 having pores of diameter equal to 0.4 µm.

The body 2 is formed by a portion 9 and a portion 10 with one nested in the other. Portion 9 has an opening 7 for introduction of the liquid while portion 10 has an opening 8 for outlet of that liquid.

Portion 9 has a first cylindrical part 15 delimiting the opening 7 on one side and on the opposite side joining a second part 16 which is also cylindrical and of diameter less than that of part 15, parts 15 and 16 being connected to each other by a transverse annular wall 17.

Adjacent the transverse wall 17 is fixed the porous support 5 and is sealed the membrane 3, which bears by its face 12 against the porous support 5 from the same side as the opening 7 (FIG. 1).

Portion 10 comprises a first cylindrical part 20 of diameter substantially equal to the diameter of the cylindrical part 15, a second cylindrical part 21 of diameter substantially equal to the diameter of the cylindrical part 16, and a third cylindrical part 22 of diameter less than the diameter of part 21 and delimiting the opening 8.

Portions 20 and 21 are connected to each other by a transverse annular wall 23 whereas portions 21 and 22 are connected to each other by a transverse annular wall 24.

Adjacent the annular wall 23 is fixed the porous support 6 and is sealed the membrane 4, which bears by its face 14 against the porous support 6, the face 13 of that membrane facing the porous support 5 (FIG. 1).

Portion 9 with membrane 3 delimits a compartment 26 for admission of the liquid to filter, portions 9 and 10 in the nested state delimiting with membranes 3 and 4 an intermediate compartment 27 whereas portion 10 with membrane 4 delimits a compartment 28 for evacuation of the liquid.

In the nested state of portion 9 in portion 10 of the body 2, the outwardly turned surface of the cylindrical part 16 faces the inner surface of the cylindrical part 20 while they bear against each other by elastic deformation so as to maintain portions 9 and 10 fastened together.

A description will now be made of the different steps of preparing a sample from a liquid to analyze which may contain eukaryote cells and bacteria whose presence it is desired to detect among those cells.

At a first step, the operator connects the cylindrical part 22 to a vacuum source (a vacuum pump for example) to place compartment 28 under reduced pressure and delivers a predetermined volume (for example 10 ml) of liquid into compartment 26.

Placing compartment 28 under reduced pressure gives rise to the placing under reduced pressure of compartment 27 such that the predetermined volume of liquid is sucked and passes through membrane 3 and support 5 to occupy compartment 27.

The pores of membrane 3 are dimensioned such that only the microorganisms of greatest size, here the eukaryote cells, are retained by that membrane, whereas the other microorganisms, here the bacteria, pass through it and porous support 5 to arrive in the filtrate occupying compartment 27.

Furthermore, the large size of the pores of membrane 3 mean that even when that membrane is wet, it remains permeable to the air (absence of bubble point phenomenon) such that the air can penetrate into compartment 27 by membrane 3.

As this membrane allows the air to pass, the filtrate contained in compartment 27 then flows through membrane 4 and support 6 to occupy compartment 28 and then leave body 2 through the outlet opening 8.

The pores of membrane 4 are dimensioned so as to retain the bacteria which it is desired to detect.

Once these operations have been carried out, the operator disconnects the vacuum source from the cylindrical part 22.

Figure 2:
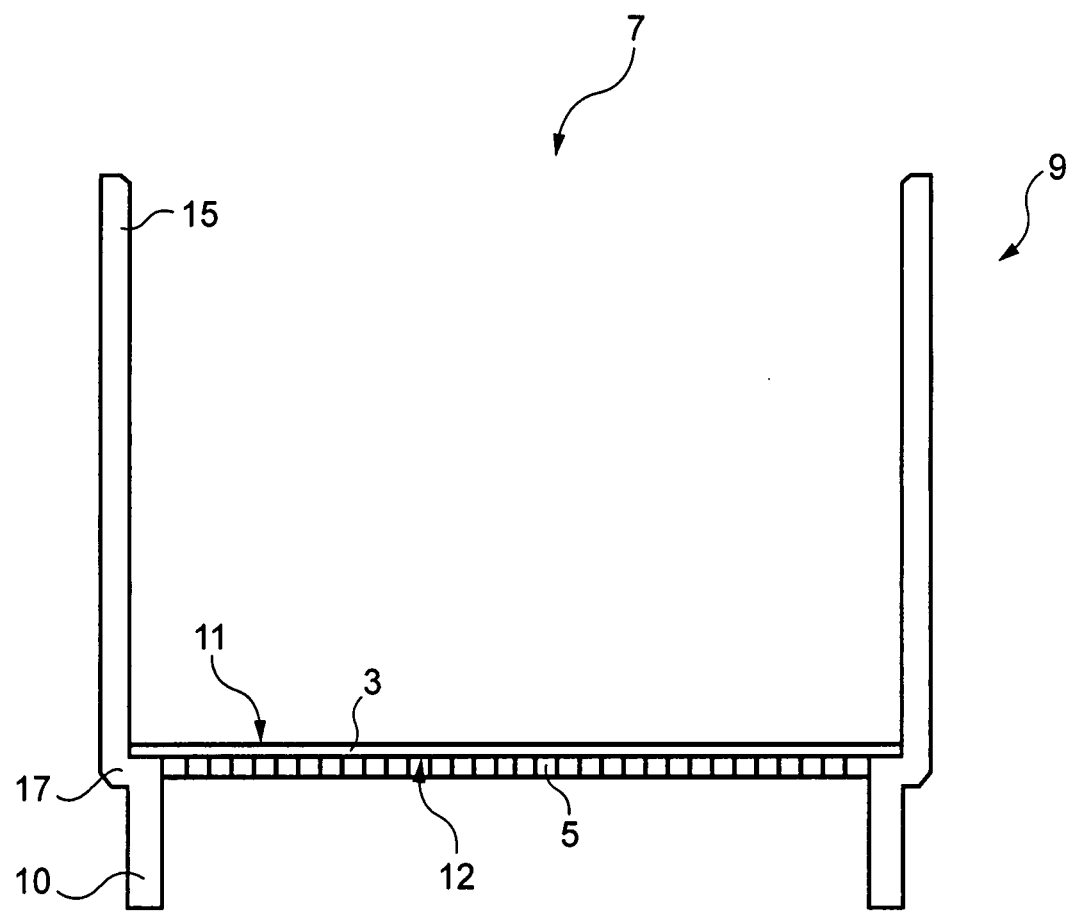
FIG. 2 is a view of the unit similar to FIG. 1 but in which the two portions of a body of that unit which were nested together have been separated.
Figure 2:
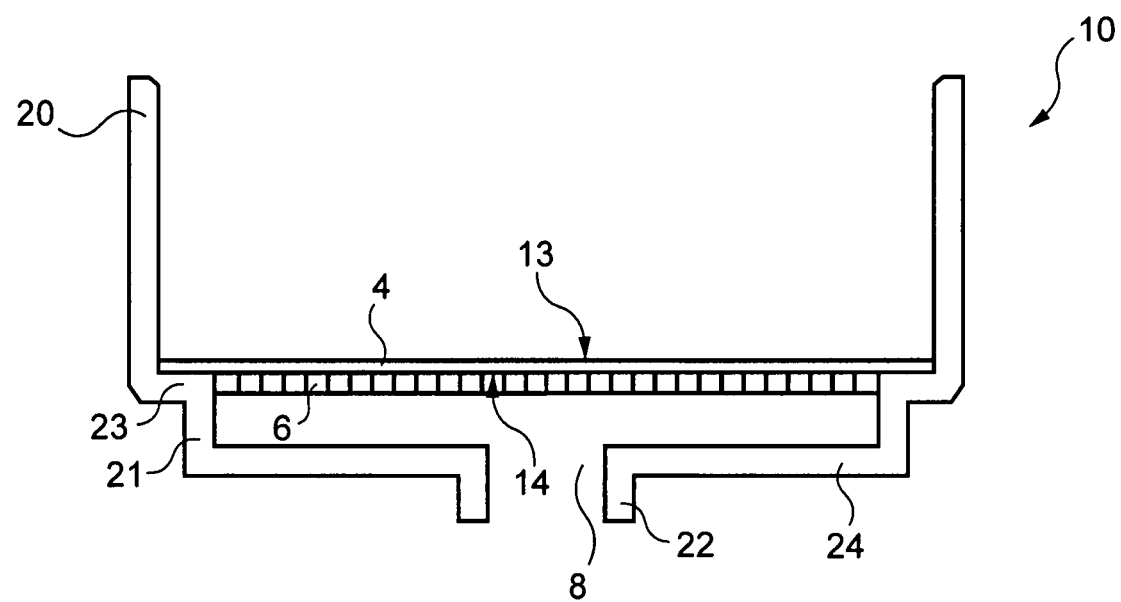

Next he separates portions 9 and 10 by sliding portion 9 with respect to portion 10 such that they disengage from each other as illustrated in FIG. 2.

Membrane 4 and in particular face 13 of that membrane on which the sample has been collected is thus rendered accessible.

It is then possible to extract that membrane to place it in contact with a gel growth medium and then to place that assembly in an incubator to incubate the bacteria.

Another solution consists of treating that membrane (after having or not having extracted it from portion 10) by depositing thereon from the face 13 side a reagent revealing the presence of the ATP of the bacteria by luminescence or another possibility is a reagent making it possible to identify the bacteria by fluorescence.

Still another solution consists of analyzing the DNA of the bacteria collected on membrane 4 by a conventional method (of PCR type, for example).

It is also possible, if it is desired to retrieve the sample independently of the membrane, to deposit on that membrane an agent for lysing bacteria.

By again connecting the unit to a source of vacuum, the lysate containing the biological material of the bacteria then passes through membrane 4 then compartment 28 to be collected in a container disposed beyond opening 8. The liquid retrieved in this container may then be analyzed by a fast microbiological detection method (by luminescence for example).

The combined use of the unit according to the invention with the fast detection methods for the microorganisms makes it possible to verify in short periods of time and on a large scale all kinds of liquid samples that may contain several types of microorganisms.

Figure 3:
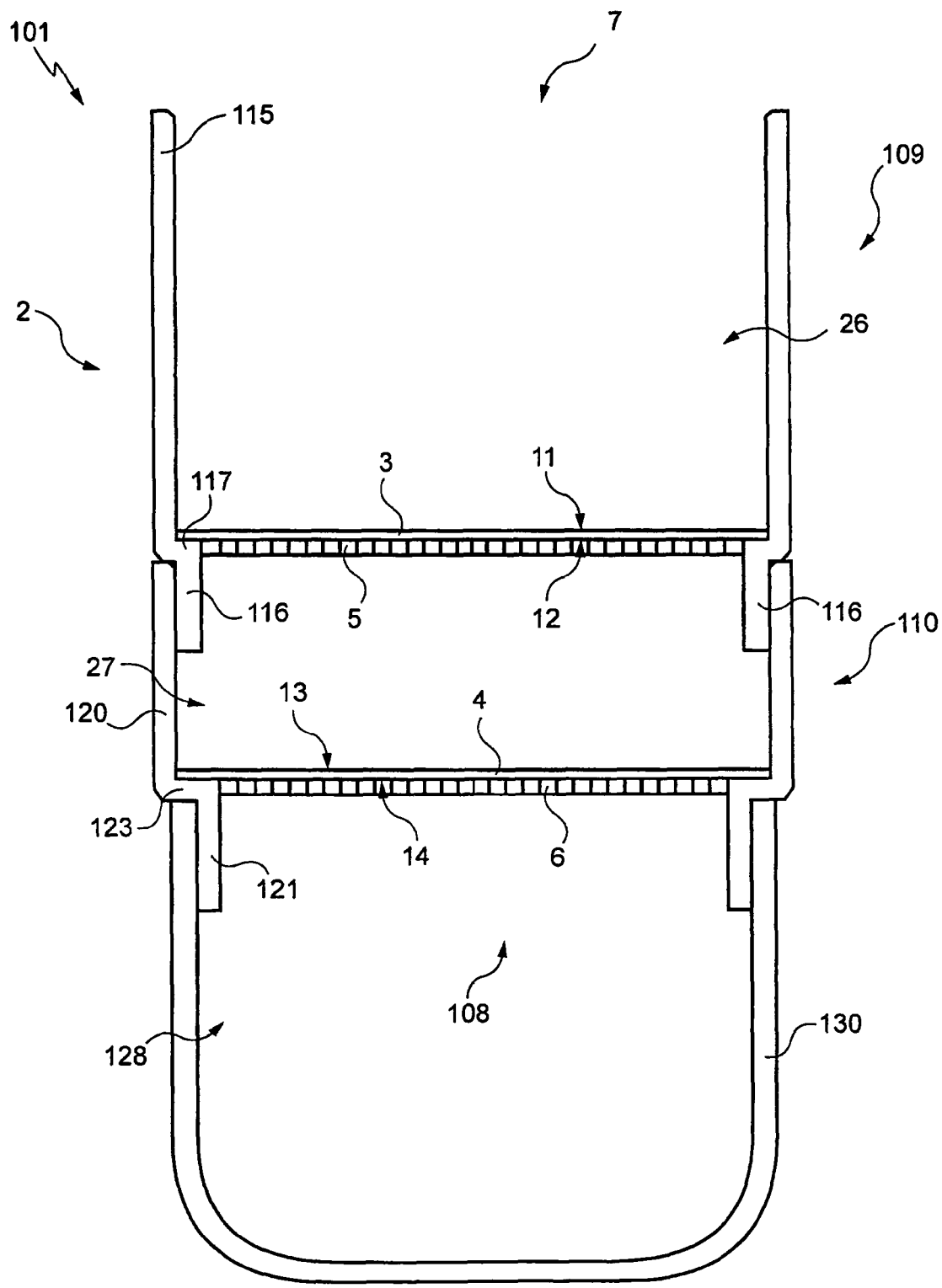
FIG. 3 is a view similar to FIG. 1 of a second embodiment of the preparation unit.

Another embodiment of the preparation unit is represented in FIG. 3.

Generally, for similar members the same references have been used, to which the number 100 has been added.

The preparation unit 101 is adapted to be placed in a centrifuge so as to make the liquid pass through the two membranes without having to place the preparation unit under reduced pressure.

In this embodiment, the annular 24 and cylindrical 22 parts have been eliminated whereas cylindrical part 121 is extended with respect to part 21 of the preceding embodiment such that it is possible to fit onto it a cup 130 belonging to body 2 to extract the second filtrate when the liquid comes out from the opening 108 or else to retrieve a lysate in that cup, once the second filtrate has been emptied, when it is desired to retrieve the sample independently from membrane 4 (by depositing a lysing agent on that membrane).

The cup is thus adapted to be separated from portion 110 (by sliding along cylindrical part 121) either to empty the second filtrate or to obtain access to the lysate in order to perform a fast microbiological detection on that lysate, for example by adding into the cup a reagent revealing the presence of ATP by luminescence.

Figure 4:
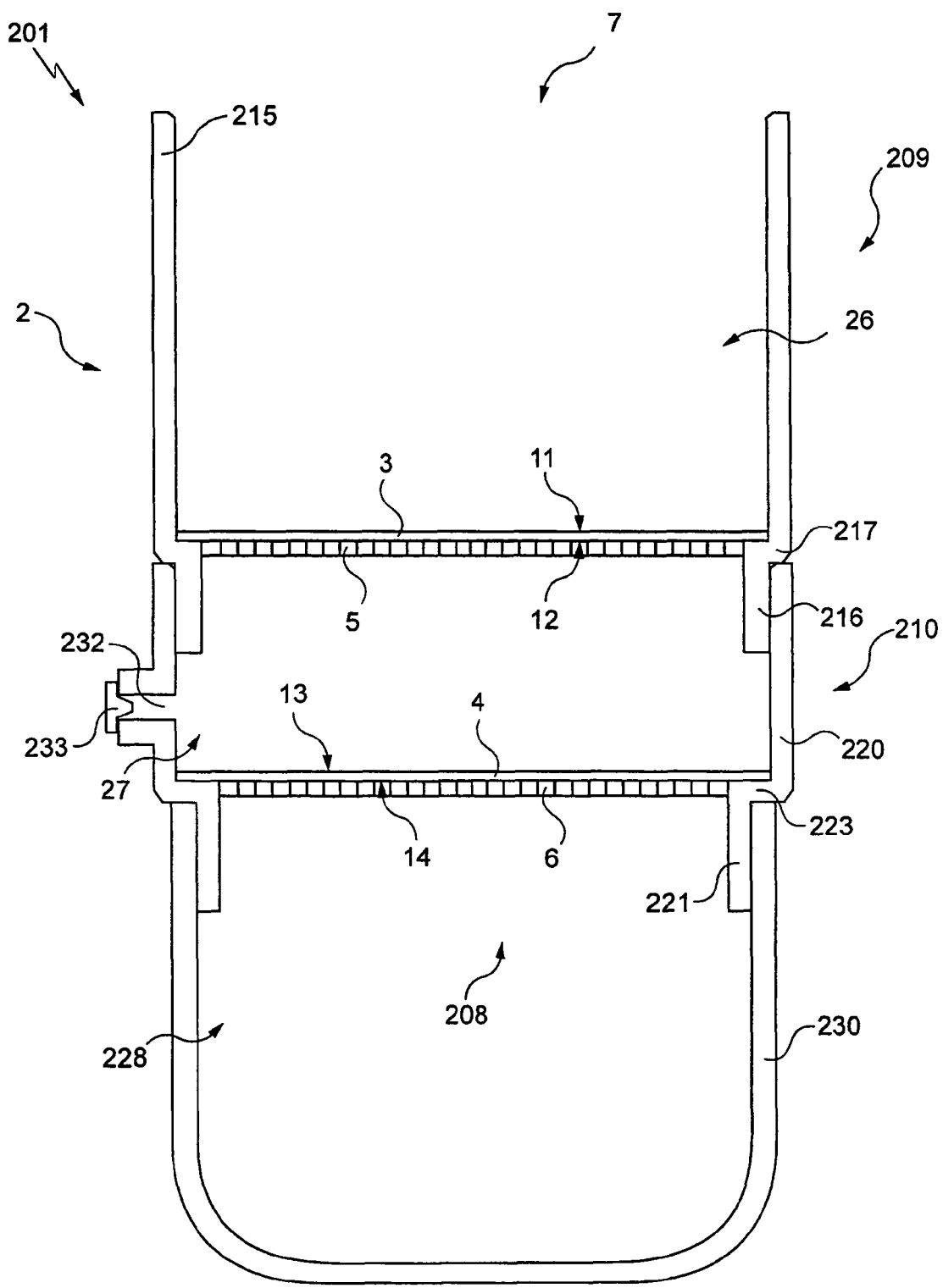
FIG. 4 is a view similar to FIG. 1 of a third embodiment of the preparation unit.

Another embodiment is represented in FIG. 4.

In this embodiment, the preparation unit 201 has a similar structure to preparation unit 101 apart from an opening 232, obturated in fluid-tight manner by a removable stopper 233, which is provided laterally in cylindrical part 220 of portion 210 of body 2.

Once the sample has been prepared and the stopper 233 removed, this opening makes it possible if needed to obtain access to compartment 27 and in particular to face 13 of membrane 3, for example to deposit a lysing agent there, without having to separate portions 209 and 210 of body 2, the biological material of the microorganisms then being retrieved in cup 230.

In a variant, the pores of membrane 4 are of diameter less than 0.1 μm so as to collect bacteria and/or viruses on the membrane.

In still another variant, the liquid is passed through membranes 3 and 4 by placing the admission chamber 26 under increased pressure for example using a piston engaged in cylindrical part 15 by leaving between the piston and the liquid a volume of air. When it is actuated, the piston gives rise to the displacement of the volume of liquid as well as the volume of air compressed between the piston and liquid, such that compartment 26 is placed under increased pressure. The liquid therefore penetrates into compartment 27 and is then flushed by the air pushed by the piston, which air in turn penetrates into compartment 27 through membrane 3 which remains permeable to air.

In a still further variant, the microorganisms to detect are not bacteria or viruses but yeasts (of sufficiently small size not to be retained by the first membrane) or molds for example.

In yet another variant, the liquid to analyze does not contain eukaryotes but other types of microorganisms (to separate from the microorganisms to detect) such as yeasts or else filamentous fungi.

In again another variant, the two portions of the body of the preparation unit snap-fit together and the separation of the portions is carried out for example by breaking the snap-fitting feet.

In still another variant, the two portions form a single piece and are connected by a frangible zone to be broken in order to separate them from each other.

In yet another variant the membrane collecting the sample is not sealed to the body of the preparation unit but is pressed against an 'O' ring seal and/or the membranes are formed of Polyethersulfone (PES), polycarbonate, polyester or another possibility is cellulose ester.

The present invention is not limited to the embodiment described and represented but covers any variant form.

The invention claimed is:

1. A method of preparing a sample for the microbiological analysis of a liquid containing microorganisms of several different types each having predetermined morphological characteristics, which method comprises the step of determining the size of undesired microorganisms in said sample;

the step of procuring a unit for preparing said sample comprising a generally tubular body within which are fixed a first and a second membrane, said body having an opening for introduction of said liquid, a first compartment between said introduction opening and said first membrane, a second compartment between said first and second membranes and a third compartment on the side of said second membrane opposite the side facing said first membrane, the step of selecting said first membrane in response to the determined size of the undesired microorganisms, to have a first pore diameter small enough to retain said undesired microorganisms and large enough to allow desired microorganisms to pass through, the step of selecting said second membrane to have a predetermined second pore diameter less than said predetermined first pore diameter of said first membrane and small enough to retain said desired microorganisms;

the step of passing a predetermined volume of said liquid from the first to the second compartment through said first membrane;

the step of passing all the filtrate, having so reached the second compartment, from the second to the third compartment through said second membrane in order to collect said sample on said second membrane with said desired microorganisms selected from said different types of microorganisms which are those of which the size is less than the predetermined pore diameter of said first membrane and greater than the predetermined pore diameter of said second membrane;

the step of retrieving said sample so collected on said second membrane for further analysis of the desired microorganisms contained in said sample;

wherein the steps of passing said liquid through said membranes are performed by centrifuging said preparation unit.

2. A method according to claim 1, wherein the step of procuring a preparation unit comprises the step of selecting a preparation unit of which the body comprises a first portion to which is fixed said first membrane and a second portion to which is fixed said second membrane, said portions being detachable from each other, and in that the step of retrieving said sample comprises the step of detaching said second portion of said body from said first portion of said body.

3. A method according to any one of claims 1 to 2, wherein the step of procuring a preparation unit comprises the step of selecting as said first membrane a membrane of pore diameter greater than 1 µm.

4. A method according to any one of claims 1 to 2, wherein the step of procuring a preparation unit comprises the step of selecting as said second membrane a membrane of pore diameter less than 0.65 µm.

5. A method according to claim 4, wherein the step of procuring a preparation unit comprises the step of selecting as said second membrane a membrane of pore diameter less than 0.1 µm.

6. The method of claim 1, wherein said further analysis comprises extracting said second membrane and placing it in contact with a gel growth medium, followed by incubating said microorganisms on said second membrane.

7. The method of claim 1, wherein said further analysis comprises treating said second membrane with a reagent capable of revealing the presence of ATP of the microorganisms on said second membrane.

8. The method of claim 1, wherein said further analysis comprises analyzing the DNA of the microorganisms on said second membrane.

* * * * *